United States Patent
Stanglmeier et al.

(10) Patent No.: US 6,890,422 B1
(45) Date of Patent: May 10, 2005

(54) OXIDIZABLE GAS COMPONENT SENSOR AND METHOD OF USING THE SENSOR

(75) Inventors: Frank Stanglmeier, Moeglingen (DE); Bernd Schumann, Rutesheim (DE); Thomas Moser, Schwieberdingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/936,847
(22) PCT Filed: Mar. 10, 2000
(86) PCT No.: PCT/DE00/00754
§ 371 (c)(1), (2), (4) Date: Jun. 4, 2002
(87) PCT Pub. No.: WO00/57168
PCT Pub. Date: Sep. 28, 2000

(30) Foreign Application Priority Data

Mar. 18, 1999 (DE) .......................................... 199 12 100

(51) Int. Cl.[7] ........................ G01N 27/419; G01N 27/41
(52) U.S. Cl. ................................ 205/783.5; 205/780.5; 205/784.5; 205/787; 204/425
(58) Field of Search ................................ 204/421–429; 205/783.5, 784.5, 784, 787, 780.5

(56) References Cited

U.S. PATENT DOCUMENTS 5,672,811 A * 9/1997 Kato et al.
5,879,525 A * 3/1999 Kato .......................... 204/424
5,985,118 A * 11/1999 Makino et al. ............. 204/426

FOREIGN PATENT DOCUMENTS

| DE | 23 04 464 | 8/1974 |
| EP | 0 791 828 | 8/1997 |
| EP | 0 831 322 | 3/1998 |

OTHER PUBLICATIONS

Ronald K. Jurgen, *Automotive Electronics Handbook*, McGraw–Hill, Inc., NY, 1999, Chap. 6, pp. 1–11.

* cited by examiner

*Primary Examiner*—Kaj K. Olsen
(74) *Attorney, Agent, or Firm*—Kenyon & Kenyon

(57) ABSTRACT

An electrochemical gas sensor determining the concentration of oxidizable gas components which has an electrochemical measuring cell having a measuring electrode and a reference electrode. Measuring electrode is made of a material which is not able, or not completely able to catalyze the establishment of gas equilibrium. In addition to the electrochemical measuring cell, at least one electrochemical pumping cell, having at least one inner pumping electrode, is provided, which, together with measuring electrode, is positioned in a measuring gas compartment. Oxygen is pumped into or out of measuring gas compartment by pumping cell, the partial pressure of oxygen in measuring gas compartment being set to a lambda value of $\geq 1.3$.

12 Claims, 1 Drawing Sheet

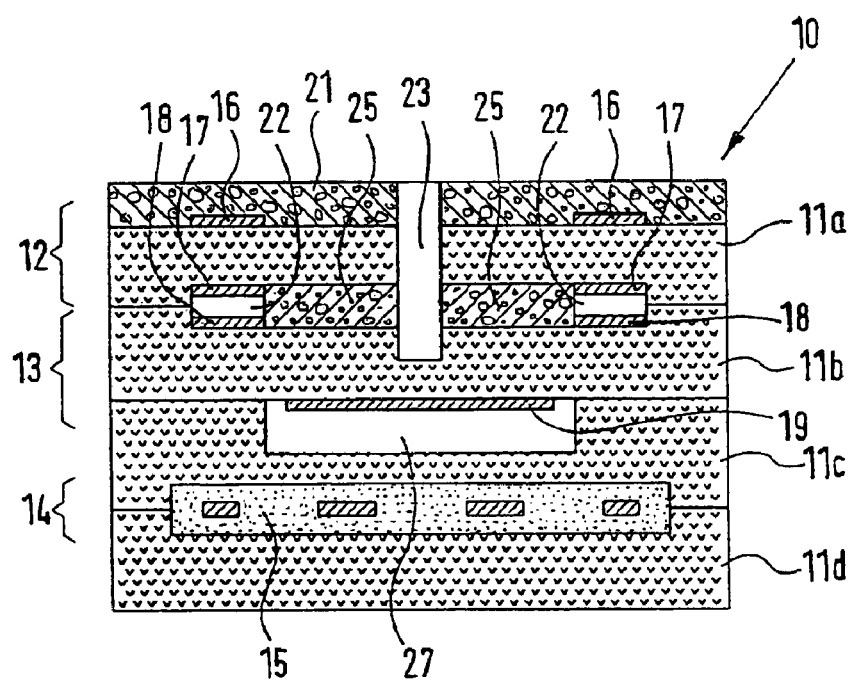

OXIDIZABLE GAS COMPONENT SENSOR AND METHOD OF USING THE SENSOR

FIELD OF THE INVENTION

The present invention relates to an electrochemical gas sensor for determining the concentration of oxidizable gas components in gas mixtures.

BACKGROUND INFORMATION

German Patent No. 23 04 464 describes an electrochemical gas having an electrode made of gold or silver which does not catalyze the establishment of equilibrium of the gas mixture, and which acts together with an electrode made of platinum which catalyzes the establishment of equilibrium in the gas to be measured (the measuring gas). The catalytically inactive electrode materials have the effect that, between the oxygen and the oxidizable or reducible gas components, respectively, a competitive reaction takes place at the electrode. Even with adjusted high lambda values, this causes the free oxygen carried along in the measuring gas hardly to react with, for example, $C_3H_6$ or CO, so that free oxygen as well as $C_3H_6$ or CO, respectively, reach the three-phase boundary at the catalytically inactive electrode. However, such a gas sensor has a considerable cross sensitivity to the oxygen also present in the gas mixture.

SUMMARY OF THE INVENTION

The gas sensor according to an embodiment of the present invention has the advantage that the cross sensitivity to oxygen can be reduced by pumping in oxygen. A further advantage is that a base sensor element, which is fully developed from a manufacturing technique point of view, can be used, which has only to be changed by a modification of the electrodes. A so-called broadband sensor is used as a base sensor element for determining the oxygen concentration, and it includes a pumping cell and a concentration cell (measuring cell), whereby a mixed potential sensor having a series-connected oxygen pumping cell is formed. The use of a standard base sensor element offers considerable cost advantages compared to sensor element construction which is specialized for each application.

The cross sensitivity to oxygen can be reduced to the utmost if the partial pressure of the oxygen, which can be set in the gas to be analyzed by the pumping cell, has a lambda value of $\geq 1.3$.

BRIEF DESCRIPTION OF THE DRAWING

The FIGURE shows a cross-section through a sensor element of the gas sensor according to an embodiment of the present invention.

DETAILED DESCRIPTION

The FIGURE shows a planar sensor element 10 of an electrochemical gas sensor, which, for example, has a plurality of solid electrolyte carrier layers 11a, 11b, 11c, and 11d that conduct oxygen ions. In this context, the solid electrolyte carrier layers 11a through 11d are designed as ceramic foils, and form a planar ceramic body after sintering. The integrated form of the planar ceramic body is produced conventionally, by laminating together the ceramic foils printed over with functional layers and subsequently sintering the laminated structure. Each of the solid electrolyte carrier layers 11a through 11d is formed from solid electrolyte material, conducting oxygen ion, such as $ZrO_2$ stabilized with $Y_2O_3$.

Sensor element 10 has an electrochemical pumping cell 12 and an electrochemical measuring cell 13 (concentration cell) as well as a resistance heater 14. The resistance heater 14 is situated between solid electrolyte carrier layers 11c and 11d, and is embedded in electrical insulation 15, e.g. made of $Al_2O_3$ Sensor element 10 is heated to the appropriate operating temperature of, e.g. 500° C., by resistance heater 14.

Pumping cell 12 has an outer pumping electrode 16 and an inner pumping electrode 17. Measuring cell 13 is formed having a measuring electrode 18 and a reference electrode 19. The outer pumping electrode 16 is covered with a porous protective layer 21 and exposed to the gas to be measured. The inner pumping electrode 17 of pumping cell 12 and measuring electrode 18 of measuring cell 13 are located opposite each other in a measuring gas compartment 22 which is in communication with the gas to be measured via a gas access hole 23. Reference electrode 19 is located in a reference gas channel, which is in communication with a reference gas, such as air.

A porous diffusion barrier 25 is arranged inside measuring gas compartment 22, in front of inner pump electrode 17 and measuring electrode 18, in the diffusion direction of the measuring gas. Porous diffusion barrier 25 constitutes a diffusion resistor with regard to the gas diffusing towards electrodes 17, 18.

The described design of sensor element 10 corresponds to a so-called broadband sensor for determining the lambda value in gas mixtures of lambda values less than or greater than 1. In the broadband sensor, all electrodes are made of a material which catalyzes the establishment of equilibrium of the gas mixture, such as platinum and platinum cermet material.

In the gas sensor of the present invention, which responds to oxidizable gases such as HC, $H_2$, CO and $NH_3$, in contrast to the broadband sensor mentioned above, at least measuring gas electrode 18 positioned in measuring gas compartment 22 is made of a material which cannot or cannot completely catalyze the establishment of equilibrium of the gas mixture. Such a material may be gold or a gold-platinum alloy, the gold proportion of the platinum-gold alloy being 0.5 to 20 weight-%, such as 10 weight-%. These materials guarantee that measuring electrode 18, positioned in measuring gas compartment 22, is selective with respect to the oxidizable gas components contained in the gas mixture.

In addition to measuring electrode 18, the further inner pumping electrode 17, positioned in measuring gas compartment 22, may be made of a material which cannot, or cannot completely catalyze the establishment of equilibrium of the gas mixture. Inner pumping electrode 17 contains a platinum-gold alloy having a gold proportion of 0.1 through 3 weight-%, such as 0.3 through 0.8 weight-%.

The materials are co-sinterable, that means, that they withstand sintering temperatures, such as 1400° C., for sintering solid electrolyte carrier layers 11a to 11d. For producing a firm layer bond between solid electrolyte carrier layers 11a to 11d and electrodes 17, 18, the latter, as also electrodes 16, 19 are made of a cermet material. Aside from the catalytically active platinum or the catalytically inactive gold or platinum-gold alloy, such cermet electrodes contain a ceramic proportion corresponding in an advantageous way to the material of the adjoining solid electrolyte carrier layers 11a to 11d.

In the operating method of the gas sensor, a pumping voltage is applied to pumping electrodes 16, 17 which is poled, according to the partial pressure of the oxygen, in such a way that, when there is a high oxygen partial pressure in the exhaust gas, oxygen is pumped out of measuring gas compartment 22, and when there is low oxygen partial pressure in the measuring gas, oxygen is pumped into measuring gas compartment 22. For this purpose, a corresponding switching arrangement is provided, which, in addition, guarantees that an essentially constant partial pressure of oxygen is maintained in measuring gas compartment 22.

Tests have shown that the cross sensitivity of the sensor to oxygen is low when there is a partial pressure of oxygen of lambda $\geq 1.3$ in measuring gas compartment 22, i.e., at measuring electrode 18. It was determined that with a partial pressure of oxygen of more than lambda $\geq 1.3$, the influence of the oxygen concentration on the measurement for determining the concentration of hydrocarbons is negligible. The measuring electrode 18 is a so-called mixed potential electrode, which catalyzes no, or at least no complete establishment of equilibrium of the gas mixture. Together with reference electrode 19, positioned in reference gas channel 27, measuring electrode 18 forms a so-called mixed potential sensor, which is particularly used for determining hydrocarbons.

The material of measuring electrode 18, which does not, or not completely catalyze the establishment of equilibrium, has the effect that a competing reaction takes place at measuring electrode 18 between the oxygen contained in the gas mixture and the reduced gas components, the hydrocarbons carried along in the gas to be measured hardly reacting with the free oxygen. In the case of a catalytically active electrode, a reaction of the hydrocarbons with the oxygen would take place. Preventing this is the function of the not catalytically active mixed potential electrode. As a result, both the free oxygen and the hydrocarbons reach the three-phase boundary of measuring electrode 18. At reference electrode 19, on the other hand, along with the reference air there is a constant, high partial pressure of oxygen.

At measuring electrode 18, the adsorbed hydrocarbons now react, and a potential difference develops between measuring electrode 18 and reference electrode 19, which can be read off as electromotive force (emf) by a measuring instrument (not shown). Thus the emf depends on the concentration of the hydrocarbons contained in the gas mixture. When there is a high concentration of hydrocarbons, there is a high potential difference, and thus a high emf. When there is a low concentration of hydocarbons, the potential difference between measuring electrode 22 and reference electrode 19 is lower, and as a result, the generated emf is lower too.

What is claimed is:

1. A method for determining a concentration of an oxidizable gas component in a gas mixture using an electrochemical gas sensor including an electrochemical measuring cell having a measuring electrode and a reference electrode, the measuring electrode having a material that is one of not able to catalyze and not able to completely catalyze an establishment of a gas equilibrium, the electrochemical gas sensor further including at least one electrochemical pumping cell having at least one inner pumping electrode, the method comprising:

positioning the at least one inner pumping electrode and the measuring electrode in a measuring gas compartment;

coupling the at least one electrochemical pumping cell to a circuit configured to apply a pumping voltage to the at least one electrochemical pumping cell, so that the at least one electrochemical pumping cell pumps oxygen into or out of the measuring gas compartment;

applying a pumping voltage to the at least one electrochemical pumping cell via the circuit such that a partial pressure of oxygen in the measuring gas compartment corresponds to a lambda value of $\geq 1.3$; and determining the concentration of the oxidizable gas component.

2. The method as recited in claim 1, further comprising setting, via the at least one pumping cell, an approximately constant partial pressure of oxygen in the measuring gas compartment.

3. The method as recited in claim 1, further comprising positioning the measuring electrode and the at least one inner pumping electrode opposite each other in the measuring gas compartment.

4. The method as recited in claim 1, further comprising providing the measuring electrode with one of gold and a platinum-gold alloy.

5. The method as recited in claim 4, wherein a gold proportion in the platinum-gold alloy is 0.5 to 20 weight-%.

6. The method as recited in claim 5, further comprising providing the at least one inner pumping electrode with a material which is one of not able to catalyze and not completely able to catalyze the establishment of the gas equilibrium.

7. The method as recited in claim 6, further comprising providing the at least one inner pumping electrode with a platinum-gold alloy having a gold proportion of 0.1 to 3 weight-%.

8. The method as recited in claim 6, further comprising providing the at least one inner pumping electrode with a platinum-gold alloy having a gold proportion of 0.3 to 0.8 weight-%.

9. The method as recited in claim 4, wherein a gold proportion in the platinum-gold alloy is approximately 10 weight-%.

10. The method as recited in claim 1, further comprising providing the reference electrode with a catalytically active material that is able to catalyze the establishment of the gas equilibrium.

11. The method as recited in claim 10, wherein the catalytically active material is platinum.

12. The method as recited in claim 1, further comprising positioning the measuring gas compartment is positioned in one layer plane.

* * * * *